United States Patent [19]

Hasegawa et al.

[11] Patent Number: 5,424,419
[45] Date of Patent: Jun. 13, 1995

[54] OXIDIZED COMPLEX COMPRISING WATER-SOLUBLE CARBOXYPOLYSACCHARIDE AND MAGNETIC IRON OXIDE

[75] Inventors: Masakatsu Hasegawa, Nagoya; Hideo Nagae, Kasugai; Yoshio Ito; Akihiro Mizutani, both of Nagoya; Kimio Hirose, Gifu; Masahiro Ohgai; Yasuji Yamashita, both of Nagoya; Nahoko Tozawa, Seto; Keiko Yamada, Ogaki; Kyoji Kito, Nagoya; Shusaburo Hokukoku, Kani, all of Japan

[73] Assignee: Meito Sangyo Kabushiki Kaisha, Aichi, Japan

[21] Appl. No.: 971,760

[22] PCT Filed: Jun. 8, 1992

[86] PCT No.: PCT/JP92/00735

§ 371 Date: Feb. 11, 1993

§ 102(e) Date: Feb. 11, 1993

[87] PCT Pub. No.: WO92/22586

PCT Pub. Date: Dec. 23, 1992

[30] Foreign Application Priority Data

Jun. 11, 1991 [JP] Japan .................. 3-166334

[51] Int. Cl.⁶ ............ C08B 37/02; A61K 31/72; A61K 49/00; A61B 5/055
[52] U.S. Cl. ................ 536/113; 514/54; 514/59; 514/60; 424/9.322; 128/653.4; 128/654; 436/173
[58] Field of Search ............ 514/54, 59, 60; 536/113; 424/4, 9, ; 128/653.4, 654; 436/173

[56] References Cited

U.S. PATENT DOCUMENTS

| | | | |
|---|---|---|---|
| 4,101,435 | 7/1978 | Hasegawa et al. | 252/62.53 |
| 4,180,567 | 12/1979 | Herb | 424/180 |
| 4,370,476 | 1/1983 | Usher et al. | 536/113 |
| 4,452,773 | 6/1984 | Molday | 424/1.1 |
| 4,599,405 | 7/1986 | Müller et al. | 536/113 |
| 4,770,183 | 9/1988 | Groman et al. | 128/654 |
| 4,788,281 | 11/1988 | Tosoni et al. | 536/113 |
| 4,829,984 | 5/1989 | Gordon | 600/12 |
| 4,985,233 | 1/1991 | Klaveness et al. | 424/9 |
| 4,986,980 | 1/1991 | Jacobsen et al. | 424/9 |

FOREIGN PATENT DOCUMENTS

| | | |
|---|---|---|
| 450092 | 10/1991 | European Pat. Off. |
| 51-151320 | 12/1976 | Japan |
| 57-42701 | 3/1982 | Japan |
| 57-109802 | 7/1982 | Japan |
| 59-13521 | 3/1984 | Japan |
| 61-233001 | 10/1986 | Japan |
| 64-500196 | 1/1989 | Japan |
| 1-235851 | 9/1989 | Japan |
| 3-134001 | 6/1991 | Japan |

OTHER PUBLICATIONS

Bremner et al., "Structural Studies on Iron-Dextran", Carbohyd. Res., 11 (1969) 77-84.
AT-208 003 (Laboratorien Hausmann A,-G.) 10 Mar. 1960.

Primary Examiner—Marian C. Knode
Assistant Examiner—Francisco C. Prats
Attorney, Agent, or Firm—Wenderoth, Lind & Ponack

[57] ABSTRACT

An oxidized complex comprising a water-soluble carboxypolysaccharide and magnetic iron oxide, which is characterized by being obtained by oxidizing a complex comprising a water-soluble carboxypolysaccharide and magnetic iron oxide. Said oxidized complex has very low toxicity, is very stable, exhibits little or no blood pressure-reducing action and has low platelets-aggregating action when administered directly into the blood vessels of animals, and is useful in medical fields such as contrast medium for magnetic resonance imaging, exothermic medium for hyperthermia and the like.

8 Claims, 2 Drawing Sheets

OXIDIZED COMPLEX COMPRISING WATER-SOLUBLE CARBOXYPOLYSACCHARIDE AND MAGNETIC IRON OXIDE

TECHNICAL FIELD

The present invention relates to a novel oxidized complex comprising a water-soluble carboxypolysaccharide and magnetic iron oxide, which is particularly useful in biological and medical fields such as contrast medium for magnetic resonance imaging, exothermic medium for hyperthermia, contrast medium for X-ray imaging and the like.

BACKGROUND ART

Ultrafine particles of magnetic iron oxide having colloidal sizes have superparamagnetism, and an aqueous sol thereof as a magnetic fluid has recently drawn attention as a contrast medium for use in magnetic resonance imaging. The aqueous sol comprising magnetic iron oxide ultrafine particles alone, however, has very low stability when a salt has been added thereto or when subjected to thermal sterilization or with time and has very high acute toxicity when administered intravenously; hence, the aqueous sol is unusable for medical treatment and efforts have been made to solve these problems.

As a means for improving the above stability and safety, it was proposed to form a complex between a polysaccharide or the like and ultrafine particles of magnetic iron oxide. For example, Japanese Patent Publication No. 13521/1984 (U.S. Pat. No. 4,101,435) discloses a complex between dextran or a carboxydextran obtained by heat-treating dextran with sodium hydroxide and ultrafine particles of magnetic iron oxide; U.S. Pat. No. 4,452,773 discloses dextran-magnetic iron oxide microspheres; and Japanese Patent Publication No. 500196/1989 (International Publication WO No. 88/00060) discloses a composition of dextran-magnetic iron oxide microspheres similar to the above, for use in in-vivo magnetic resonance imaging for the organs and tissues of animals (reference is made to Comparative Example 1 described later). Of these, a carboxydextran-magnetic iron oxide ultrafine particles complex, in particular, is remarkably improved in various stabilities and acute toxicity. However, it was confirmed that these complexes and microspheres each as an aqueous sol, when administered into blood vessels, incur significant reduction in blood pressure, leading to death in some cases.

Hence, the present inventors made an extensive study. As a result, the present inventors found that an oxidized complex obtained by treating a water-soluble carboxypolysaccharide-magnetic iron oxide ultrafine particles complex with an oxidizing agent such as oxygen gas or the like shows little or no blood pressure-reducing action without substantially affecting the properties possessed by the raw complex, such as magnetic property, metabolic property, tissue specificity and the like, and further can significantly reduce the platelets-aggregating action considered to be connected with blood pressure reduction. The present invention has been completed based on the above finding.

DISCLOSURE OF THE INVENTION

According to the present invention, there is provided an oxidized complex comprising a water-soluble carboxypolysaccharide and magnetic iron oxide, which is characterized by being obtained by oxidizing a complex comprising a water-soluble carboxypolysaccharide and magnetic iron oxide.

The oxidized complex comprising a water-soluble carboxypolysaccharide and magnetic iron oxide, provided by the present invention, when being in the form of an aqueous sol, has very low toxicity and excellent stability, shows little or no blood pressure-reducing action unlike conventional complexes when administered directly into the blood vessels of animals, has low platelets-aggregating action, has excellent safety as drug, and can be suitably used in a medical field as, for example, a contrast medium for nuclear magnetic resonance imaging (hereinafter abbreviated to MRI), a exothermic medium for hyperthermia and a carrier for drug delivery.

Detailed description is made hereinafter on the oxidized complex comprising a water-soluble carboxypolysaccharide and magnetic iron oxide (hereinafter referred to as oxidized complex, in some cases) of the present invention.

The oxidized complex of the present invention can be obtained by oxidizing a complex between a water-soluble carboxypolysaccharide (hereinafter abbreviated to CPS) and ultrafine particles of iron oxide. This complex, which is a direct starting material of the oxidized complex of the present invention, is known per se and can be prepared by, for example, a process described in Japanese Patent Publication No. 13521/1984 (U.S. Pat. No. 4,101,435).

The CPS, which is a component of the complex usable in production of the present oxidized complex, is a water-soluble polysaccharide having one carboxyl group at the reducing end of a polyaccharide molecule. The process for production thereof can be exemplified by a process which comprises heat-treating a water-soluble polysaccharide with an alkali, particularly sodium hydroxide, and a process which comprises oxidizing only the terminal reducing group of a water-soluble polysaccharide selectively with an oxidizing agent such as iodine-sodium hydroxide, sodium hypochlorite or the like. More specifically, the CPS can be obtained, for example, by adding sodium hydroxide to an aqueous polysaccharide solution and heat-treating the mixture at about 30-about 100° C., preferably at about 60-about 100° C. for 0.5-6 hours. The thus produced CPS is ordinarily desired to be purified, and the purification can be conducted by a per se known method, for example, by one or a combination of precipitation using a poor solvent, dialysis, ultrafiltration, ion exchange using a cation or anion exchange resin, electrodialysis, etc. The thus obtained CPS is considered to have one D-glucometasaccharinic acid residue per molecule [reference is made to Carbohyd. Res., 11 (1969) , 77-84].

The CPS can also be obtained, for example, by adding to an aqueous polysaccharide solution an oxidizing agent such as iodine-sodium hydroxide, sodium hypochlorite or the like and subjecting the mixture to an oxidation treatment at about 10-about 60° C., preferably at about 20-about 40° C. for 0.5-16 hours. Then, the CPS can be purified in the same manner as above.

The CPS usable in the present invention is preferably a CPS obtained by an alkali treatment, and the number-average molecular weight thereof can be in the range of generally about 500-about 300,000, preferably about 1,000-about 50,000, more preferably about 1,500-about 20,000. In the above alkali treatment or oxidation treatment, the degree of conversion from polysaccharide to CPS is higher when the amount of alkali or oxidizing agent is larger, the treating temperature is higher and the treating time is longer; and the conversion degree can generally be [100(P-C)/P] % wherein the reducing saccharide of polysaccharide is expressed by P % and the reducing saccharide of treated material is expressed by C %. In the present invention, there can be used a CPS whose conversion degree is generally about 30% or more, preferably about 50% or more, more preferably about 80% or more.

As the polysaccharide used, there can be mentioned a water-soluble polysaccharide such as glucose polymers (e.g. dextran, starch, glycogen, pullulan), galactose polymers (e.g. agarose, galactan) and xylose polymers (e.g. xylan). Of these, preferable are dextran, starch and pullulan and particularly preferable is dextran.

The process for preparing a complex (hereinafter referred to as raw complex, in some cases) usable in the production of the present oxidized complex, can be largely divided into a first process which comprises reacting a previously prepared aqueous sol comprising magnetic iron oxide ultrafine particles alone, with a CPS, and a second process which comprises synthesizing a complex in one step in the presence of a CPS.

In the first process, first an aqueous sol comprising magnetic iron oxide ultrafine particles alone is prepared. The method for preparing this aqueous sol, can be exemplified by an alkali co-precipitation method or an ion exchange resin method.

In the alkali co-precipitation method, for example, an about 0.1-about 2 M aqueous solution containing a ferrous salt of a mineral acid and a ferric salt of a mineral acid at a molar ratio of about 1:3 to about 2:1 is mixed with a base such as NaOH, KOH, NH$_4$OH or the like so as to give a pH of about 7-about 12; the mixture is as necessary aged with heating; then, the resulting magnetic iron oxide is separated, water-washed and redispersed in water; to the resulting dispersion is added a mineral acid such as hydrochloric acid or the like until the dispersion comes to have a pH of about 1-about 3; thereby, an aqueous sol of magnetic iron oxide can be obtained.

Meanwhile, in the ion exchange resin method, for example, an about 0.1-about 2 M aqueous solution containing a ferrous salt and a ferric salt at a molar ratio of about 1:2 is added to a slurry of a strongly basic exchange resin with stirring with the pH being kept at about 8-about 9; then, a mineral acid such as hydrochloric acid or the like is added until the pH of the mixture becomes about 1-about 3; thereafter, filtration is made to remove the resin and obtain an aqueous sol of magnetic iron oxide. As necessary, these aqueous sols can be purified and/or concentrated by dialysis, ultrafiltration, centrifugation or the like. The thus-obtained aqueous sol of magnetic iron oxide and aqueous CPS solution are mixed so that the weight ratio of iron and CPS becomes about 1:1 to about 1:6 although the ratio is not strictly restricted, and they are reacted with heating. The appropriate concentration of magnetic iron oxide in the reaction mixture, which is not strictly restricted, either, is generally about 0.1-about 10 W/V %, preferably about 1-about 5 W/V % in terms of iron concentration. The reaction can be conducted generally at a temperature from room temperature to about 120° C. for about 20 minutes to about 10 hours, and generally heating of about 1 hour under refluxing is sufficient.

Next, purification and adjustment is conducted. It can be conducted by one or a combination of per se known methods. For example, there is repeated a procedure of conducting ultrafiltration to separate the unreacted CPS and low-molecular compounds from a formed complex, whereby an aqueous complex sol having a desired purity and concentration can be obtained. Or, to the resulting mixture obtained is added a solvent such as methanol, ethanol, acetone or the like (each of these is a poor solvent to the complex contained in the reaction mixture) to predominantly precipitate the formed complex contained in the reaction mixture; the precipitate is separated and redissolved in water; the resulting solution is subjected to dialysis against running water and, as necessary, concentrated under vacuum; thereby, an aqueous complex sol having a desired purity and concentration can be obtained. In this case, it is possible to incorporate, in the middle of and/or after the above procedure, a step of pH adjustment, centrifugation and/or filtration.

The particle diameters of the obtained complex itself are generally in the range of about 20-about 400 nm, and the particle diameters of magnetic iron oxide in the complex are generally in the range of about 5-about 30 nm. Further, the magnetization of the complex at 1 T is generally in the range of about 20-about 150 emu per g of iron.

In the second process for complex preparation, a complex is obtained in one step by mixing an aqueous mixed iron salts solution of an ferrous salt of a mineral acid and a ferric salt of a mineral acid with an aqueous base solution in the presence of a CPS and reacting the mixture. The second process can further be classified, depending upon the addition order, into (A) a process which comprises adding an aqueous mixed iron salts solution into an aqueous CPS solution and then adding an aqueous base solution and then reacting; (B) a process which comprises adding an aqueous base solution to an aqueous CPS solution and then adding an aqueous mixed iron salts solution and then reacting; (C) a process which comprises adding to an aqueous base solution a mixture of an aqueous CPS solution and an aqueous mixed iron salts solution; (D) a process which comprises adding to an aqueous mixed iron salts solution a mixture of an aqueous CPS solution and an aqueous base solution; and so forth. These processes (A), (B), (C) and (D) differ only in the addition order and do not differ substantially in other conditions.

The preparation of the aqueous mixed iron salts solution can be conducted by dissolving a ferrous salt and a ferric salt in an aqueous medium at a molar ratio of about 1:4 to about 3:1, preferably about 1:3 to about 1:1. The concentration of the aqueous iron salts solution can be varied over a wide range, but is appropriately in the range of generally about 0.1-about 3 M, preferably about 0.5-2 M.

As the iron salts, there can be mentioned, for example, salts with mineral acids such as hydrochloric acid, sulfuric acid, nitric acid and the like. As the base, there can be used at least one base selected from alkali metal hydroxides (e.g. NaOH, KOH), amines (e.g. ammonia, triethylamine, trimethylamine), etc. The concentration of the aqueous base solution can also be varied over a wide range, but is appropriately in the range of generally about 0.1-about 10 N, preferably about 1-about 5 N. The amount of the base used can be such that the pH of the reaction mixture after components addition becomes almost neutral to about 12, that is, the normality ratio of the iron salts and the base becomes about 1:1 to about 1:1.5.

The amount of the CPS used can be about 1-about 15 times, preferably about 3-about 10 times the weight of iron in iron salts. The concentration of the aqueous CPS solution is not strictly restricted, either, but is appropriately in the range of generally about 1-about 40 W/V %, preferably about 5-about 30 W/V %. Addition and mixing of the individual solutions can be conducted with stirring, at a temperature from room temperature to about 100° C.; as necessary, a base or an acid is added for pH adjustment; then, the mixture is reacted at a temperature of about 30-about 120° C. for about 10 minutes to about 5 hours, generally for about 1 hour under refluxing. The thus obtained reaction mixture is purified in the same manner as in the above-mentioned first process and, as necessary, there can be conducted pH adjustment, concentration and filtration.

The above-obtained complex is desired to have, by itself, particle diameters of generally about 10-about 300 nm, and the magnetic iron oxide in the complex is convenient to have particle diameters of generally about 2-about 20 nm. Further, the complex can generally have a magnetization at 1 T of about 10-about 150 emu per g of iron.

In any of the above processes, the ratio of the CPS and magnetic iron oxide in raw complex obtained depends upon the diameters of magnetic iron oxide, the molecular weight of CPS, etc. and can be varied over a wide range; however, the raw complex can generally contain the CPS in an amount of about 0.1-about 5 parts by weight, preferably about 0.2-about 3 parts by weight per part by weight of the iron in magnetic iron oxide.

In any of the first and second processes for preparation of raw complex, 50 mole % or less of the ferrous salt can be replaced by other bivalent metal salt(s), for example, salt(s) of one or more metals such as magnesium, calcium, manganese, nickel, cobalt, copper, zinc, strontium and barium and the like; and the raw complex produced by such replacement is also included in the present invention.

The oxidized complex of the present invention can be produced by oxidizing the above-mentioned CPS-magnetic iron oxide raw complex. In the raw complex used in the present invention, the magnetic iron oxide has particle diameters of generally about 2-about 30 nm, preferably about 4-about 15 nm; the raw complex has a magnetization at 1 T of about 10-about 150 emu, preferably about 30-about 150 emu per g of iron; the weight ratio of CPS to iron in complex can be about 0.1-about 5, preferably about 0.2-about 3; and the raw complex is preferably produced by the second process.

In the present invention, the oxidation can be conducted by allowing an appropriate oxidizing agent to act on the aqueous sol of raw complex. The oxidizing agent is preferably such that it can oxidize magnetic iron oxide to reduce the content of bivalent iron but does not substantially oxidize or decompose the CPS. The oxidizing agent can be exemplified by peroxides (e.g. hydrogen peroxide and ozone) and oxidizing gases (e.g. oxygen gas and a mixed gas of oxygen gas and an inert gas), and the oxidizing gases are preferred.

In the oxidation using a peroxide, the peroxide can be exemplified by hydrogen peroxide and ozone, with hydrogen peroxide being preferred. In the oxidation reaction, the concentration of the aqueous sol of raw complex is not particularly restricted, but is appropriately in the range of generally about 0.1-about 4 M, preferably about 0.5-about 2 M as iron. It is preferable that a peroxide be added to said aqueous sol in an amount of about 0.2-about 4 times, preferably 0.3-about 2 times the moles of bivalent iron and the resulting mixture be subjected to a reaction at about 0-about 80° C., preferably about 15-about 40° C. for about 10 minutes to about 24 hours, preferably about 1-about 5 hours preferably with stirring. As necessary, after the addition of a decomposing agent for peroxide, such as sodium sulfite or the like, purification and/or adjustment is conducted in the same manner as mentioned in the preparation of raw complex, whereby an aqueous sol of oxidized complex according to the present invention, having a desired purity, concentration and pH, can be obtained. In this case, particularly when purification is conducted by ultrafiltration, if the CPS content in complex becomes low, addition of CPS to a desired CPS concentration is preferable for improved stability. The aqueous sol obtained may be dried by a per se known method, preferably a freeze-drying method to obtain an oxidized complex of powdery form. The particle diameters of obtained oxidized complex itself, the particle diameters of magnetic iron oxide in oxidized complex and the magnetization of oxidized complex at 1 T do not change substantially and are about the same with those of raw complex.

Meanwhile, in the oxidation using an oxidizing gas, the oxidizing gas can be exemplified by oxygen gas, air and a mixed gas of oxygen gas and an inert gas such as nitrogen gas, argon gas, helium gas or the like. Oxygen gas and air are particularly preferable. As desired, it is possible to further use a catalyst such as platinum, palladium, iridium, a compound thereof or the like. In the oxidation reaction, the concentration of aqueous sol of raw complex is not particularly restricted, but is appropriately in the range of about 0.1-about 4 M, preferably about 0.5-about 2 M as in the oxidation using a peroxide. The oxidation reaction can be conducted, with stirring, in an oxidizing gas and, as desired, under pressure and/or under application of an ultrasonic wave.

The oxidation reaction is depends upon main factors such as the properties of raw materials, the concentration of oxidizing gas, the temperature, the pH, the time, etc. When the reaction proceeds too much, the oxidized complex formed is aggregated. The optimum conditions for the oxidation reaction can be easily determined experimentally. Generally, the reaction can be conducted at a temperature from room temperature to about 120° C., preferably about 60-about 100° C. for about 0.5 hours-about 3 days, preferably about 2-about 16 hours with the final pH adjusted to about 3-about 8, preferably about 4-about 6. Then, purification and/or adjustment is made as necessary in the same manner as mentioned above, whereby an aqueous sol of oxidized complex according to the present invention, having a desired purity, concentration and pH can be obtained. In this case, particularly when purification is conducted by ultrafiltration, if the CPS content in the complex becomes low, addition of CPS to a desired CPS concentration is preferable as in the oxidation using a peroxide. The aqueous sol obtained may be dried in the same manner as in the oxidation using a peroxide, preferably by a freeze-drying method to obtain an oxidized complex of powdery form. The use of an oxidizing gas, preferably oxygen gas is preferable because the occurrence of side reactions is lower as compared with the case using a peroxide. The shape and physical properties of the oxidized complex obtained are not different substantially from those of the raw complex used, as in the case using a peroxide.

The thus-obtained oxidized complex of the present invention has substantially the same properties as the raw complex used, except that the oxidized complex has a lower bivalent iron content and a property not affecting blood pressure, i.e. high safety. The properties of the present oxidized complex are described hereinafter in more detail. Unless otherwise specified, the measurement methods for the properties of the oxidized complex and the properties of the material complex are the same.

In the oxidized complex of the present invention, the ratio of magnetic iron oxide to CPS depends mainly upon that of the raw complex used and also on the oxidation conditions and the purification conditions, but the ratio is generally 50 to 100% of that of the raw complex. When the ratio is too small, the stability of the oxidized complex is improved, for example, by adding the same CPS as used in the raw complex to the aqueous sol of oxidized complex in such an amount that the CPS content in said sol becomes about 0.5-about 4 parts by weight, preferably about 0.8-about 2 parts by weight per part by weight of iron.

Incidentally, the iron content in complex in the present specification (this iron includes the total iron derived from magnetic iron oxide) is a value determined by colorimetry using o-phenanthroline, based on, for example, the method described in Analytical Chem., 22 (1950) 326. That is, concentrated hydrochloric acid is added to an aqueous sol or powder of complex to decompose the iron contained therein, into chlorides; the reaction mixture is diluted appropriately and used as a test solution; to 2 ml of the test solution are added 1 ml of 10% hydroxylamine hydrochloride and then 7 ml of a solution of 0.1% of o-phenanthroline in 0.4 M acetate buffer (pH 4); the resulting mixture is measured for absorbance at a wavelength of 510 nm. A iron standard solution and the water used for measurement are also measured for absorbance in the same manner. The iron content in complex is determined from the ratio of these absorbances.

The CPS content in complex is a value determined by the sulfuric acid-anthrone method based on the method described in Analytical Chem., 25, 1656 (1953). That is, the solution after hydrochloric acid-decomposition, used in the above determination of iron content, is diluted appropriately and added to a sulfuric acid-anthrone reagent to develop a color, and the colored solution is measured for absorbance. The CPS, used in complex production, as a standard substance is allowed to develop a color in the same manner and the colored solution is also measured for absorbance in the same manner. The CPS content in complex is determined from the ratio of the two absorbances.

The proportion of bivalent iron to total iron in the oxidized complex of the present invention varies depending upon the oxidation conditions, the particle diameters of magnetic iron oxide, etc., but is in the range of generally about 0-about 10%, preferably about 2-about 7%. Meanwhile, said proportion in the raw complex is generally about 10-about 30%. Incidentally, the proportion of bivalent iron to total iron is determined in the same manner as used in the above-mentioned determination of the iron content in complex, for example, purging with nitrogen to prevent the oxidation by air during determination and further using 1 M potassium fluoride in place of 10% hydroxylamine hydrochloride.

Figure 1:
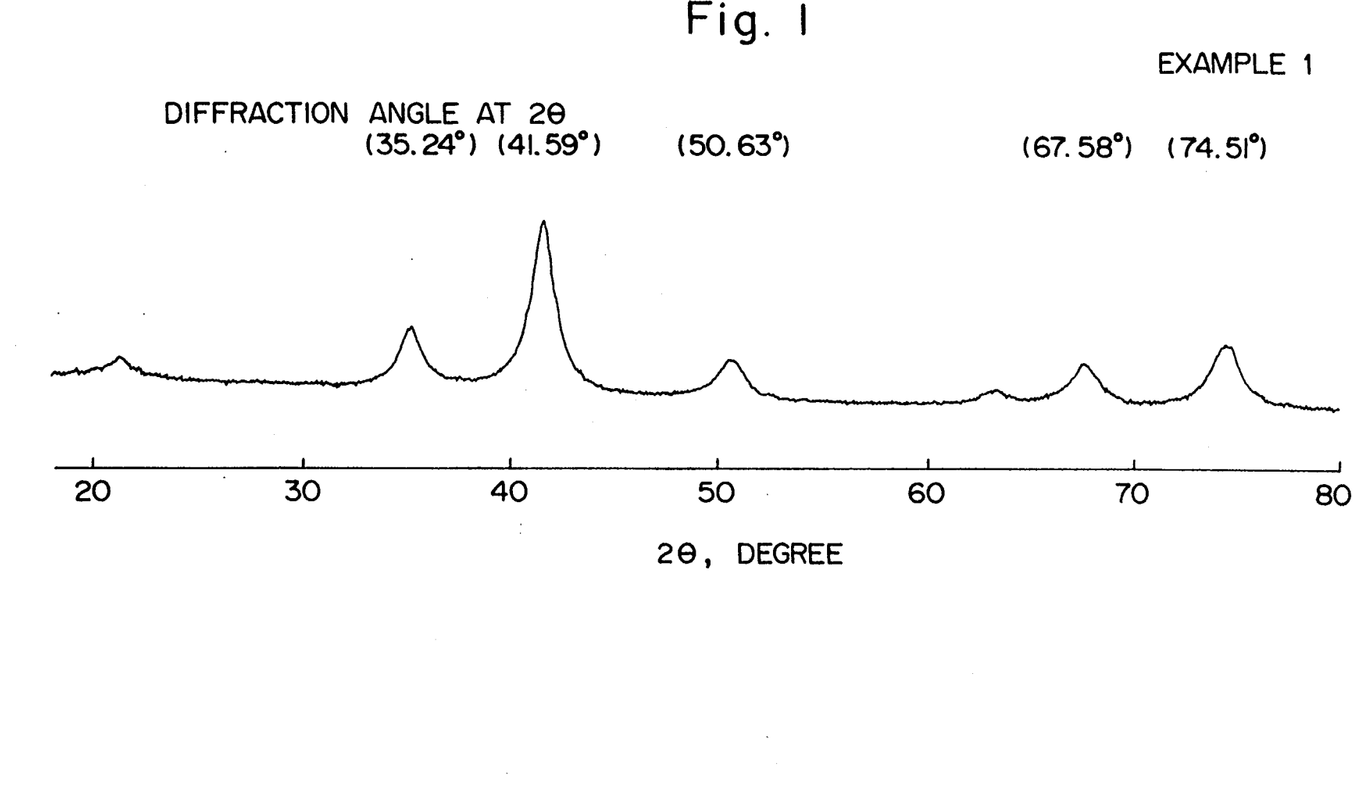
FIG. 1 is an X-ray diffraction pattern obtained for the oxidized complex produced in Example 1, using a powder X-ray diffractometer (target=Co, wavelength=1.790 Å).
Figure 2:
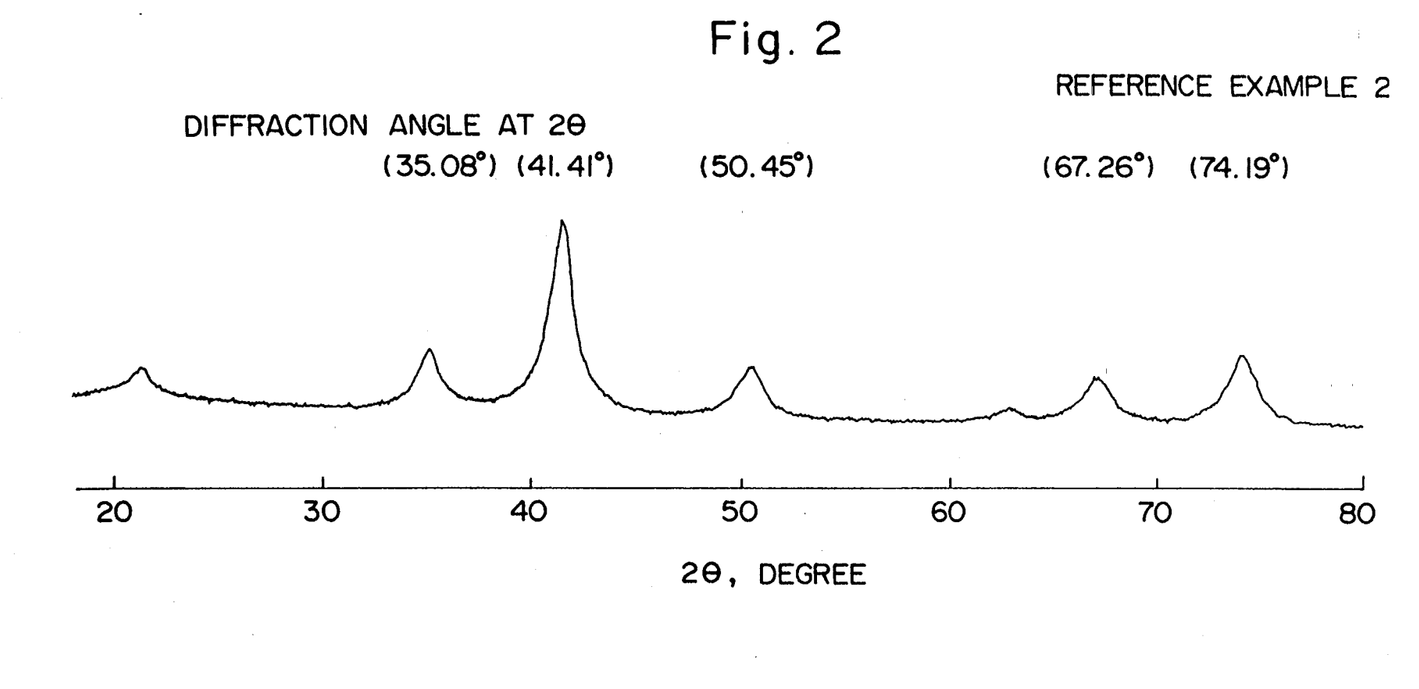
FIG. 2 is an X-ray diffraction pattern obtained for the material complex produced in Reference Example 2, using a powder X-ray diffractometer (target=Co, wavelength=1.790 Å).

When the oxidized complex of the present invention and the raw complex therefor are subjected to X-ray diffraction using a powder X-ray diffractometer (target=Co, wavelength=1.790Å), the diffraction patterns of the two complexes are broad but agree with that of magnetite ($Fe_3O_4$) as a standard sample. As to their diffraction angles, that of the raw complex agrees with or is close to that of magnetite while that of the oxidized complex is shifted slightly to a higher angle side. These facts indicate that the basic skeleton of magnetic iron oxide in raw complex is not changed by oxidation but the lattice constant (length of crystal unit) becomes smaller by oxidation. Incidentally, these results shows that the oxidized complex of the present invention contains magnetic iron oxide as a key element from a viewpoint of X-ray diffraction, and the present invention covers the magnetic iron oxide which includes even those having crystal water or a hydroxyl group on the surface.

The diffraction peak obtained by X-ray diffraction becomes broader, i.e. smaller as the diameters of magnetic particles in complex become smaller. Therefore, when the diameters of magnetic iron oxide particles in complex are 0.1 μm or less, the particle diameters can be measured by X-ray diffraction. That is, the particle diameters can be calculated in accordance with the following Scherrer's formula, for the maximum peak in X-ray diffraction.

$$D = k\lambda/\beta \cdot \cos\theta$$
$$\beta = \sqrt{B^2 - b^2}$$

wherein
D=particle diameter (Å)
k=constant, 0.9
μ=wavelength of X-rays (1,790
θ=Bragg angle (°)
B=half width of sample (radian)
b=half width of standard sample (radian)

Incidentally, the standard sample is a magnetite having particle diameters of 1 μm or more. The above-obtained value agrees fairly well with the value determined using a transmission electron microscope.

The particle diameters of the present oxidized complex itself are values measured by a dynamic light-scattering method [reference is made to, for example, Polymer J., 13, 1037–1043 (1981)]. The oxidized complex of the present invention can have a diameter in the range of generally about 10-about 500 nm, preferably about 20-about 200 nm.

The oxidized complex of the present invention is not a mere mixture but a compound of magnetic iron oxide and a CPS. This can be understood from, for example, the fact that when the aqueous sol of oxidized complex of the present invention is subjected to fractionation using a gel column, the elution peak is seen at a higher-molecular side relative to the elution site of the CPS contained in said complex and the analysis of the peak detects the presence of both a saccharide and iron in the peak, or the fact that in the course of production of said aqueous sol of oxidized complex, when purification is made using an ultrafilter membrane having a pore size capable of passing particles smaller than said oxidized complex, the ratio of saccharide and iron in the aqueous sol remaining unfiltered converges gradually to a certain constant value.

The magnetic properties (e.g. magnetization and coercive force) of the oxidized complex of the present invention can be determined by drawing a magnetization-magnetic field curve (a so-called M-H curve) at room temperature using a vibrating sample magnetometer. The magnetization at 1 T of the present Oxidized complex is in the range of generally about 10-about 150 emu, preferably about 30-about 150 emu per g of iron. Further, the coercive force of the present oxidized complex is about 30 Oe or less and has superparamagnetism substantially.

The $T_2$ relaxivity of the present oxidized complex in aqueous sol form can be determined by diluting the present oxidized complex with water to prepare aqueous sols of various concentrations, drawing the resonance curves for proton of water, of said sols and the water used for dilution by using CW-NMR of 60 MHz (magnetic field of about 1.4 T), determining the half width of peak, i.e. $\Delta \nu_{\frac{1}{2}}$ (unit=Hz), calculating $1/T_2$ (unit=sec)=$\pi \cdot \Delta \nu_{\frac{1}{2}}$, plotting on a graph the relation between $1/T_2$ and the iron concentration (unit=mM) in aqueous sol of test sample, and calculating the inclination of straight line by a least squares method, and has a unit of $(\text{sec} \cdot \text{mM})^{-1}$. The thus-obtained $T_2$ relaxivity of the present oxidized complex in aqueous sol form is in the range of generally about 5-about 1,000 $(\text{sec} \cdot \text{mM})^{-1}$, preferably about 10-about 500, more preferably about 20-about 300 $(\text{sec} \cdot \text{mM})^{-1}$.

When the aqueous sol of raw complex is administered to, for example, rabbits intraveneously, as in administration of conventional known magnetic iron oxide agents, the rabbits have a significantly reduced blood pressure in few to several minutes, leading to death in some cases. However, quite unexpectedly, no or very small reduction in blood pressure occurs with the oxidized complex of the present invention, and the present oxidized complex shows significant improvement.

It was also found that the oxidized complex of the present invention has very low platelets-aggregating action. That is, when each of the aqueous sol of raw complex and the aqueous sol of oxidized complex is administered to, for example, rabbits intravenously and there is determined the ratio of the number of platelets in blood 5 minutes after the administration, to the number of platelets right before the administration, i.e. the residual ratio (%) of platelets, the ratio is generally about 1-about 20% in the raw complex and about 20-about 100% in the oxidized complex of the present invention. Thus, the present oxidized complex shows significant improvement.

Further, the oxidized complex of the present invention, as compared with conventional know unoxidized complexes or microspheres, shows very different interaction with bovine albumin. That is, as shown in Test 3 described later, when a sol of a conventional known complex and a sol of the present oxidized complex are each mixed with an aqueous sol of bovine albumin, the conventional known complex interacts with the albumin and invites severe aggregation while the present oxidized complex has very low interaction with the albumin and incurs substantially no or very slight aggregation.

When the oxidized complex of the present invention and the material complex are compared with respect to the acute toxicity $LD_{50}$ when administered to mice intravenously, the present oxidized complex gives an acute toxicity of about 15-about 80 mmol/kg as iron, which is about the same as that of the raw complex.

Also when the present oxidized complex and the material complex are compared by administering each of them to mice intravenously in an amount of 5 mmol/kg as iron, excising their lungs 5 minutes thereafter, and inspecting the lungs histopathologically, the present oxidized complex gives the same inspection results as the material complex. That is, neither embolus nor other abnormalities are observed in any of the tissue samples subjected to hematoxylin-eosine dyeing and Berlin blue dyeing.

It is known that at least the magnetic iron oxide portion of the aqueous sol of oxidized complex or material complex tends to cumulate rapidly after intravenous administration, in organs of well developed reticuloendothelial system such as liver, spleen, bone marrow and the like and, in a small administration amount (e.g. 0.1 mmol/kg or less as iron), most or possibly nearly all of the complex administered cumulate in the Kupffer's cells of liver. By measuring, based on the above fact, the degree of magnetism of liver using CW-NMR, the metabolic properties of the oxidized complex and the material complex were evaluated.

That is, the aqueous sol of oxidized complex or material complex is administered to rats intravenously in an amount of 0.1 mmol/kg as iron; the livers of rats are measured for $1/T_2$ (unit=$\text{sec}^{-1}$) in the same manner as for $T_2$ relaxation ability, for example, 1 hour, 2 hours, 4 hours, 1 day, 3 days, 7 days and 14 days after the administration; correction is made using the $1/T_2$ values of livers of rat group of no administration; from the relation between the corrected $1/T_2$ and the time after administration is calculated the metabolic property of each complex as half life. The half life of a preferred embodiment of the present invention, for example, the oxidized complex shown in Example 1 is about 4 days while the half life of the material complex shown in Reference Example 2 is also about 4 days. Thus, it is appreciated that the oxidation of complex does not affect the metabolic property of complex.

The oxidized complex of the present invention can be safely used in biological and medical fields as, for example, an iron-supplementing agent, a contrast medium for X-ray imaging, a contrast medium for MRI, a exothermic medium for thermotherapy and a carrier used for blood stream measurement or for concentrated administration of drug to affected part using a magnetic field. The present oxidized complex can be used particularly advantageously in administration into blood vessels.

The oxidized complex of the present invention which can be preferably used as a contrast medium for MRI varies widely depending upon the administration method and the tissue to which the oxidized complex is applied, but is preferably such that the number-average molecular weight of CPS is in the range of generally about 500-about 300,000 preferably about 1,000-about 50,000, more preferably about 1,500-about 20,000, the particle diameters of magnetic iron oxide are in the range of about 2-about 30 nm, preferably about 5-about 15 nm, and the $T_2$ relaxation ability is in the range of generally about 5-about 1,000 $(\text{sec} \cdot \text{mM})^{-1}$, preferably about 10-about 500 $(\text{sec} \cdot \text{mM})^{-1}$, more preferably about 20-about 300 $(\text{sec} \cdot \text{mM})^{-1}$.

When the present oxidized complex is used as a contrast medium for MRI, the oxidized complex is preferably used in the form of an aqueous sol. In this case, the concentration of the oxidized complex can be varied over a wide range but can be in the range of, for example, generally about 1 mM to about 4 M, preferably about 0.01-about 2 M as iron. In the preparation of an aqueous sol, it is possible to add, for example, inorganic salts such as sodium chloride and the like; monosaccharides such as glucose and the like; sugar alcohols such as mannitol, sorbitol and the like; organic acid salts such as acetic acid salt, lactic acid salt, citric acid salt, tartaric acid salt and the like; and physiologically acceptable adjuvants such as phosphate buffer agent, tris buffer agent and the like. It is also possible to add an aqueous sol of oxidized complex to various Ringer's solutions.

The amount of the present oxidized complex used as a contrast medium for MRI differs depending upon the site of patient to be inspected, but is in the range of generally about 1 μmol/kg to about 10 mmol/kg body weight, preferably about 2 μmol/kg to about 1 mmol/kg body weight as iron. As the administration method, there are mentioned, for example, injection or infusion into veins, arteries, bladder, muscles, subcutaneous parts, etc., and oral administration and direct intraintestinal administration are possible in some cases. When a preferred embodiment of the present oxidized complex is administered, for example, intravenously, a large portion of the oxidized complex cumulates in reticuloendothelial systems, particularly the liver in a relatively short length of time, for example, within few to several hours, making it possible to conduct MRI for liver favorably. In this case, when the liver has a lesion site (e.g. a cancerous site) of low reticuloendothelial function, no oxidized complex or only a very small amount of the oxidized complex cumulates in the lesion site unlike in other normal sites; thus, the lesion site can be easily detected by MRI. Incidentally, the oxidized complex of the present invention is effective not only as a contrast medium for $T_2$ image but also as a contrast medium for $T_1$ image.

EXAMPLES

The present invention is hereinafter described more specifically by way of Reference Examples, Examples, etc.

Reference Example 1

In 350 ml of water was dissolved 105 g of a carboxydextran obtained by subjecting a dextran having a molecular weight of 4,000 to a thermal treatment with sodium hydroxide (the conversion of dextran=95%). Thereto was added an aqueous solution obtained by dissolving 13.6 g of ferrous chloride tetrahydrate in 140 ml of a 1 M aqueous ferric chloride solution (corresponding to 37.8 g of ferric chloride hexahydrate) in a nitrogen gas stream. Thereto was further added 242 ml of a 3 N aqueous sodium hydroxide solution with heating and stirring. The resulting mixture was adjusted to pH 7.0 by adding 6 N hydrochloric acid and then refluxed for 1 hour and 30 minutes. After cooling, the reaction mixture was subjected to centrifugation at 2,100 x G for 30 minutes. 93%, based on the volume of the supernatant liquid, of ethanol was added to precipitate a complex. Centrifugation was conducted at 2,100 x G for 10 minutes. The precipitate obtained was dissolved in water and the solution was subjected to dialysis with running water for 16 hours. The dialyzate was adjusted to pH 7.2 with sodium hydroxide, concentrated under reduced pressure, and filtered through a membrane filter (pore size=0.2 μm) to obtain 190 ml of an intended aqueous sol of complex of Reference Example 1 (iron concentration=56 mg/ml). Particle diameter of magnetic iron oxide=8.8 nm, particle diameter of complex obtained=70 nm, weight ratio of CPS/iron=1.08, magnetism at 1 T=91 emu/g iron, $T_2$ relaxivity=230 $(mM.sec)^{-1}$, proportion of bivalent iron in total iron=21%

Reference Example 2

1,050 g of the carboxydextran used in Reference Example 1 was dissolved in 3,500 ml of water. Thereto was added an aqueous solution obtained by dissolving 136 g of ferrous chloride tetrahydrate in 1,400 ml of a 1 M aqueous ferric chloride solution (corresponding to 378 g of ferric chloride hexahydrate) in a nitrogen gas stream. Thereto was further added 2,420 ml of a 3 N aqueous sodium hydroxide solution with heating and stirring. The resulting mixture was adjusted to pH 7.1 by adding 6 N hydrochloric acid and then refluxed for 2 hours. After cooling, the reaction mixture was subjected to centrifugation at 2,100 x G for 30 minutes. The supernatant liquid was filtered through a membrane filter (pore size=0.2 μm). Water was added to the filtrate to obtain a total volume of 10 l. It was subjected to ultrafiltration (fractionation molecular weight: 100,000 daltons) to concentrate to 1.5 l. The concentrate was subjected to ultrafiltration (fractionation molecular weight: 100,000 daltons) while adding water thereto, until the amount of the liquid discharged became 12 l. To the retentate solution was added a required amount of the same carboxydextran as above so that the weight ratio of carboxydextran and iron became 1:1. Then, the mixture was adjusted to pH 7.0 with sodium hydroxide and subjected to centrifugation at 2,100 x G for 1 hour and 30 minutes. The supernatant liquid was filtered through a membrane filter (pore size=0.2 μm) to obtain 1.9 l of an intended aqueous sol of complex of Reference Example 2 (iron concentration=57 mg/ml). Particle diameter of magnetic iron oxide=8.6 nm, particle diameter of complex obtained=64 nm, weight ratio of CPS/iron=1.03, magnetism at 1 T=89 emu/g iron, $T_2$ relaxivity=220 $(mM.sec)^{-1}$, proportion of bivalent iron in total iron =23%

Reference Example 3

580 ml of water was added to 1,000 ml of Amberlite IRA-410 (an ion exchange resin produced by Rohm and Haas Co.), to obtain a slurry. To the slurry was added a mixture of 200 ml of a 1 M aqueous ferric chloride solution and 100 ml of a 1 M aqueous ferrous chloride solution at 30° C. or below with stirring while the pH of the resulting mixture was being maintained at 8.0-8.7. Successively, concentrated hydrochloric acid was added to obtain pH 1.5. The mixture was stirred for 1 hour at the same pH. Then, filtration was conducted to separate a sol from the ion exchange resin, and the sol was subjected to dialysis with running water for 10 hours to obtain an aqueous sol of magnetic iron oxide (pH=3.5, iron concentration=12.8 mg/ml). To 980 ml of this sol was added 100 g of the carboxydextran used in Reference Example 1, and the mixture was refluxed for 40 minutes. After cooling, 840 ml of ethanol was added. The mixture was subjected to centrifugation at 2,100 x G for 10 minutes. The resulting precipitate was dissolved in water. The solution was subjected to dialysis with running water for 16 hours. To the dialyzate obtained was added a required amount of the same carboxydextran as above. The mixture was adjusted to pH 7.2 with an aqueous sodium hydroxide solution and concentrated under reduced pressure. The concentrate was filtered using a membrane filter (pore size=0.45 μm) to obtain 210 ml of an intended aqueous sol of complex of Reference Example 3 (iron concentration=54 mg/ml). Particle diameter of magnetic iron oxide=6.5 nm, particle diameter of complex obtained=80 nm, weight ratio of CPS/iron=0.86, magnetism at 1 T=85 emu/g iron, $T_2$ relaxivity=195 $(mM.sec)^{-1}$, proportion of bivalent iron in total iron =9.0%.

Reference Example 4

A dextran having a molecular weight of 20,000 was heat-treated with sodium hydroxide to obtain a carboxydextran at a conversion of 90%. 167 g of the carboxydextran was dissolved in 700 ml of water. Thereto was added an aqueous solution obtained by dissolving 27.2 g of ferrous chloride tetrahydrate in 280 ml of a 1 M aqueous ferric chloride solution (corresponding to 75.6 g of ferric chloride hexahydrate) in a nitrogen gas stream. Thereto was further added 484 ml of a 3 N aqueous sodium hydroxide solution with heating and stirring. The resulting mixture was adjusted to pH 7.0 by adding 6 N hydrochloric acid and then refluxed for 1 hour and 30 minutes. After cooling, the reaction mixture was subjected to centrifugation at 2,100 x G for 30 minutes. 55%, based on the volume of the supernatant liquid, of ethanol was added to precipitate a complex. Centrifugation was conducted at 2,100 x G for 10 minutes. The resulting precipitate was dissolved in water. Thereto was added 57%, based on the volume of the solution, of ethanol to reprecipitate a complex. Centrifugation was conducted at 2,100 x G for 10 minutes. The resulting precipitate was dissolved in water and the solution was subjected to dialysis with running water for 16 hours. The dialyzate was adjusted to pH 7.2 with sodium hydroxide and concentrated under reduced pressure. The concentrate was filtered through a membrane filter (pore size=0.2 μm) to obtain 390 ml of an intended aqueous sol of complex of Reference Example 4 (iron concentration=56 mg/ml). Particle diameter of magnetic iron oxide=7.8 nm, particle diameter of complex obtained=63 nm, weight ratio of CPS/iron=1.12, magnetism at 1 T=85 emu/g iron, $T_2$ relaxivity=195 $(mM.sec)^{-1}$, proportion of bivalent iron in total iron=16%

Reference Example 5

A dextrin (starch) having a molecular weight of 10,000 was heat-treated with sodium hydroxide to obtain a carboxydextrin at a conversion of 73%. 147 g of the carboxydextrin was dissolved in 700 ml of water. Thereto was added an aqueous solution obtained by dissolving 7.2 g of ferrous chloride tetrahydrate in 280 ml of a 1 M aqueous ferric chloride solution (corresponding to 75.6 g of ferric chloride hexahydrate) in a nitrogen gas stream. Thereto was further added 484 ml of a 3 N aqueous hydroxide solution with heating and stirring. The resulting mixture was adjusted to pH 7.0 by adding 6 N hydrochloric acid and then refluxed for 1 hour. After cooling, the reaction mixture was subjected to centrifugation at 2,100 x G for 30 minutes. Thereto was added ethanol in an amount of 0.74 time that of the supernatant liquid to precipitate a complex. The precipitate was redissolved in water and the solution was subjected to dialysis with running water for 16 hours. The dialyzate was adjusted to pH 7.2 with sodium hydroxide and concentrated under reduced pressure. The concentrate was filtered through a membrane filter (pore size=0.45 μm) to obtain 390 ml of an aqueous sol of material complex of Reference Example 5 (iron concentration =56 mg/ml). Particle diameter of magnetic iron oxide=5.1 nm, particle diameter of complex obtained=53 nm, weight ratio of CPS/iron=2.04, magnetization at 1 T=45 emu/g iron, $T_2$ relaxivity=40 $(mM.sec)^{-1}$, proportion of bivalent iron in total iron=13%

Comparative Example 1

75 g of a dextran having a molecular weight of 20,000 was dissolved in a mixture of 56 ml of water and 100 ml of a 25% aqueous ammonia water. Thereto was added, slowly in 5 minutes with vigorous stirring, 150 ml of a solution containing 20.5 g of ferrous chloride hexahydrate and 11.3 g of ferric chloride tetrahydrate. The resulting slurry was subjected to ultrasonic treatment for 20 minutes, then stirred at 80° C. for 30 minutes, and adjusted to pH 7.6 with hydrochloric acid, followed by heating (100° C. for 1 hour) and cooling. The cooled material was subjected to centrifugation at 2,100 x G for 30 minutes. 320 ml of ethanol was added to 420 ml of the supernatant liquid to precipitate a complex. Centrifugation was conducted at 2,100 x G for 10 minutes. The resulting precipitate was dissolved in 400 ml of water. Thereto was added 205 ml of ethanol to reprecipitate a complex. Centrifugation was conducted at 2,100 x G for 10 minutes. The resulting precipitate was dissolved in water, and the solution was subjected to dialysis with running water for 16 hours. The dialyzate was adjusted to pH 7.6 with sodium hydroxide and concentrated under reduced pressure. The concentrate was filtered through a membrane filter (pore size=0.45 μm) to obtain 115 ml of an intended aqueous sol of microspheres (iron concentration=57 mg/ml). Particle diameter of oxidized magnetic iron oxide=7.4 nm, particle diameter of microspheres obtained=96 nm, weight ratio of CPS/iron=1.25, magnetization at 1 T=90 emu/g iron, $T_2$ relaxivity 220 $(mM.sec)^{-1}$ proportion of bivalent iron in total iron=14%

EXAMPLE 1

1,050 g of the same carboxydextran as used in Reference Example 1 was dissolved in 3,500 ml of water in accordance with the manner of Reference Example 2. Thereto was added an aqueous solution obtained by dissolving 136 g of ferrous chloride tetrahydrate in 1,400 ml of a 1 M aqueous ferric chloride solution (corresponding to 378 g of ferric chloride hexahydrate) in a nitrogen gas stream. There was further added 2,420 ml of a 3 N aqueous sodium hydroxide solution with heating and stirring. The mixture was adjusted to pH 7.1 by adding 6 N hydrochloric acid and refluxed for 2 hours. After cooling, the reaction mixture was subjected to centrifugation at 2,100 x G for 30 minutes. The supernatant liquid was filtered through a membrane filter (pore size=0.2 μm). Water was added to the filtrate to obtain a total volume of 10 l. It was subjected to ultrafiltration (fractionation molecular weight=100,000 daltons) to concentrate to 1.5 l. Then, the concentrate was subjected to ultrafiltration (fractionation molecular weight=100,000 daltons) while adding water to the concentrate, until the amount of the liquid discharged became 12 l, whereby 1.9 l of an aqueous sol of composite was obtained in which the weight ratio of carboxydextran and iron was 0.4:1 and the iron concentration was 57 mg/ml. The aqueous sol was adjusted to pH 7.5 with sodium hydroxide, after which the aqueous sol was oxidized with oxygen gas at 95° C. for 3 hours and 30 minutes with the pH being controlled with sodium hydroxide so as not to become 4.2 or below. After cooling, the reaction mixture was concentrated to 1 l by ultrafiltration (fractionation molecular weight=100,000 daltons). Then, the concentrate was subjected to ultrafiltration (fractionation molecular weight=100,000 daltons) while adding water thereto, until the amount of the liquid discharged became 12 l. To the retentate solution was added a required amount of the same carboxydextran as above so that the weight ratio of carboxydextran and iron became 1:1. The mixture was adjusted to pH 7.0 with sodium hydroxide and subjected to centrifugation. The supernatant liquid was filtered through a membrane filter (pore size=0.2 μm) to obtain 1.75l of an intended aqueous sol of complex of Example 1 (iron concentration=56 mg/ml). Particle diameter of oxidized magnetic iron oxide=8.5 nm, particle diameter of complex obtained=67 nm, weight ratio of CPS/iron=1.08, magnetization at 1 T=87 emu/g iron, T relaxivity=210 (mM.sec)$^{-1}$, proportion of bivalent iron in total iron=3.4%

EXAMPLE 2

1l of the aqueous sol of complex (iron concentration=56 mg/ml) prepared in accordance with Reference Example 1 was oxidized with oxygen gas at 95° C. for 7 hours. After cooling, the resulting material was treated in the same manner as in Example 1 to obtain 950 ml of an intended aqueous sol of complex of Example 2 (iron concentration=55 mg/ml). Particle diameter of oxidized magnetic iron oxide=8.8 nm, particle diameter of complex obtained=68 nm, weight ratio of CPS/iron=1.05, magnetization at 1 T=88 emu/g iron, $T_2$ relaxivity=220 (mM.sec)$^{-1}$, proportion of bivalent iron in total iron=3.3%

EXAMPLE 3

A synthesis reaction was conducted in accordance with Reference Example 2. The reaction mixture after refluxing was filtered. To the filtrate was added water to obtain 10 l of a complex solution. The solution was concentrated to 1.5 l by ultrafiltration (fractionation molecular weight=100,000 daltons) to obtain an aqueous sol of complex in which the weight ratio of carboxydextran and iron was 1.4:1 and the iron concentration was 56 g/ml. One liter of the aqueous sol was oxidized with oxygen gas at 95° C. for 7 hours. After cooling, the resulting material was treated in the same manner as in Example 1 to obtain 960 ml of an intended aqueous sol of complex of Example 3 (iron concentration=56 mg/ml). Particle diameter of oxidized magnetic iron oxide=8.6 nm, particle diameter of complex obtained=69 nm, weight ratio of CPS/iron=1.07, magnetization at 1 T=86 emu/g iron, $T_2$ relaxivity=220 (mM. sec)$^{-1}$, proportion of bivalent iron in total iron=3.6%

EXAMPLE 4

300 ml of the aqueous sol of complex (iron concentration=56 mg/ml) prepared in accordance with Reference Example 4 was oxidized with oxygen gas at 95° C. for 3 hours and 30 minutes in the same manner as in Example 1. After cooling, the resulting material was subjected to dialysis with running water for 16 hours. The dialyzate was adjusted to pH 7.2 with sodium hydroxide and concentrated under reduced pressure. The concentrate was filtered through a membrane filter (pore size=0.2 μm) to obtain 285 ml of an intended aqueous sol of complex of Example 4 (iron concentration=55 mg/ml). Particle diameter of oxidized magnetic iron oxide=7.7 nm, particle diameter of complex obtained=78 nm, weight ratio of CPS/iron=0.97, magnetization at 1 T=84 emu/g iron, $T_2$ relaxivity=205 (mM.sec)$^{-1}$, proportion of bivalent iron in total iron=1.7%

EXAMPLE 5

300 ml of the aqueous sol of complex (iron concentration=56 mg/ml) prepared in accordance with Reference Example 3 was oxidized with oxygen gas at 90° C. for 3 hours in the same manner as in Example 1. After cooling, the resulting material was subjected to dialysis with running water for 16 hours. To the dialyzate was added a required amount of the same carboxydextran as contained in the dialyzate, so that the weight ratio of carboxydextran and iron became 1:1. The mixture was adjusted to pH 7.2 with sodium hydroxide and concentrated under reduced pressure. The concentrate was filtered through a membrane filter (pore size=0.2 μm) to obtain 285 ml of an aqueous sol of complex of Example 5 (iron concentration=54 mg/ml). Particle diameter of oxidized magnetic iron oxide=6.4 nm, particle diameter of complex obtained=88 nm, weight ratio of CPS/iron=1.10, magnetism at 1 T=85 emu/g iron, $T_2$ relaxivity=220 (mM.sec)$^{-1}$, proportion of bivalent iron in total iron=2.1%

EXAMPLE 6

To 500 ml of the aqueous sol of complex (iron concentration=56 mg/ml) prepared in accordance with Reference Example 2 was added 6.7 ml of 35% hydrogen peroxide at room temperature. The mixture was stirred for 2 hours. Thereto was added 13 g of sodium sulfite. The mixture was subjected to dialysis with running water for 16 hours. The dialyzate was adjusted to pH 7.2 with sodium hydroxide and concentrated under reduced pressure. The concentrate was filtered through a membrane filter (pore size=0.2 μm) to obtain 450 ml of an intended aqueous sol of complex of Example 6 (iron concentration=56 mg/ml). Particle diameter of oxidized magnetic iron oxide=8.7 nm, particle diameter of complex obtained=58 nm, weight ratio of CPS/iron=0.76, magnetization at 1 T=89 emu/g iron, $T_2$ relaxivity=200 (mM.sec)$^{-1}$, proportion of bivalent iron in total iron=5.3%

EXAMPLE 7

300 ml of the aqueous sol of complex obtained in Reference Example 5 was oxidized with oxygen gas at 95° C. for 3 hours and 30 minutes with the pH of the reaction mixture being controlled so as not to become 4.3 or below. After cooling, the resulting material was subjected to dialysis with running water for 16 hours. The dialyzate was treated in the same manner as in Example 4 to obtain 290 ml of an intended aqueous sol of oxidized complex of Example 7 (iron concentration=55 mg/ml). Particle diameter of oxidized iron oxide=5.6 nm, particle diameter of complex obtained=45 nm, weight ratio of CPS/iron=1.53, magnetization at 1 T=43 emu/g iron, $T_2$ relaxivity=37 $(mM.sec)^{-1}$, proportion of bivalent iron in total iron=3.4%

TEST 1

Each of the aqueous sols of complexes produced in Reference Examples 1-5, Comparative Example 1 and Examples 1-7 was subjected to a blood pressure test. The test animals were rabbits each weighing 2.5-3 kg. A cannula connected to a mercury manometer by a silicone tube was inserted into the carotid of each rabbit, and the movement of mercury caused by the change of the rabbit's blood pressure was recorded on a soot paper via a lever with a glass-made float. Each test solution was prepared by diluting each of the above-mentioned aqueous sols with a physiological saline solution so that the complex concentration after dilution became 10 mg/ml as iron, and was administered into the auricular vein of each rabbit in an amount of 10 mg iron/kg body weight. The results of blood pressure measurement are shown in Table 1.

TEST 2

Each of the aqueous sols of complexes produced in Reference Examples 1-5, Comparative Example 1 and Examples 1-7 was tested for the effect on number of platelets. The test animals were rabbits each weighing 2-3 kg. A control blood was taken from each rabbit. Then, each test solution was administered to rabbits intravenously in an amount of 5 mg/0.5 ml/kg as iron. 5 minutes and 60 minutes after the administration, blood collection was made from each rabbit; EDTA was added to each blood collected, by the Brecher Cronkite method; the EDTA-added blood was diluted 101-fold with a 1% ammonium oxalate solution, then placed in a hematocytometer, and measured for the number of platelets, using a phase-contrast microscope. The results of the measurement of platelets number are shown in Table 1 each as a ratio of said platelets number to the platelets number of control blood, i.e. a residual ratio.

TABLE 1

Results of blood pressure measurement and results of platelets number measurement

| No. of Complex | Blood pressure | Platelets number (residual ratio %) Time after administration | |
|---|---|---|---|
| | | 5 minutes | 1 hour |
| Reference Example 1 | Reduced by 36 mmHg | 3 | 9 |
| Reference Example 2 | Reduced by 44 mmHg | 4 | 12 |
| Reference Example 3 | Reduced by 31 mmHg | 6 | 10 |
| Reference Example 4 | Reduced by 49 mmHg | 2 | 8 |
| Reference Example 5 | Reduced by 26 mmHg | 15 | 63 |
| Comparative Example 1 | Reduced by 50 mmHg | 1 | 7 |
| Example 1 | Not reduced | 68 | 105 |
| Example 2 | Not reduced | 57 | 101 |
| Example 3 | Not reduced | 52 | 83 |
| Example 4 | Not reduced | 56 | 90 |
| Example 5 | Not reduced | 20 | 60 |
| Example 6 | Not reduced | 38 | 85 |
| Example 7 | Not reduced | 66 | 90 |

TEST 3

Each of the aqueous sols of complexes produced in Reference Examples 1-5, Comparative Example 1 and Examples 1-7 was examined for the interaction with bovine albumin (a product of Wako Pure Chemical Industries, Ltd., first-grade reagent). Each aqueous sol of complex was diluted 100-fold with a McIlvaine buffer solution (disodium hydrogenphosphate-citric acid buffer solution, pH 3.4); the resulting diluted solution (iron concentration=0.55 mg/ml) was mixed with an equal volume of a 1% aqueous albumin solution; the mixture was allowed to stand for 60 minutes in a constant-temperature bath of 60° C. The reaction mixture was allowed to cool to room temperature and measured for transmittance at a wavelength of 800 nm. As the control, there was used a solution obtained by diluting each aqueous sol of complex with distilled water alone (neither buffer solution nor aqueous albumin solution was used) to a measurement concentration, and the transmittance of the control was take as 100%. The results are shown in Table 2.

TABLE 2

| Interaction with albumin | |
|---|---|
| No. of complex | Transmittance (%) |
| Reference Example 1 | 3 |
| Reference Example 2 | 2 |
| Reference Example 3 | 15 |
| Reference Example 4 | 2 |
| Reference Example 5 | 2 |
| Comparative Example 1 | 10 |
| Example 1 | 83 |
| Example 2 | 92 |
| Example 3 | 96 |
| Example 4 | 96 |
| Example 5 | 94 |
| Example 6 | 73 |
| Example 7 | 96 |

TEST 4

Each of the aqueous sols of complexes produced in Reference Examples 1-5 and Examples 1-7 was subjected to in-vivo MRI. That is, each aqueous sol of complex was intravenously administered to Wister-strain rats in those livers Novikoff tumor had been transplanted, in an amount of 20 µmol as metal, and photographs of MR images were taken by the spin echo method using a MRI apparatus for animals, produced by Sisco Co. of California, USA, under the conditions of a repeating time of 400 msec and an echo time of 25 msec.

In the MR images before administration of aqueous sol of complex, the focus of tumor was unclear, and its size and shape and even the position could not be ascertained in any rat.

Meanwhile in the MR images after administration of the aqueous sols of complexes produced in Reference Examples 1-5, the position, shape and size of the focus of tumor in liver could be clearly ascertained in each rat.

Also in the MR images after administration of the aqueous sols of complexes produced in Examples 1-7, as in the cases of administration of the aqueous sols of complexes produced in Reference Examples 1-5, the position, shape and size of the focus of tumor in liver could be clearly ascertained in each rat.

INDUSTRIAL APPLICABILITY

As described above, the oxidized complex of the present invention has very low toxicity and excellent safety, shows little or no blood pressure-reducing action when administered directly into the blood vessels of animals, has low platelets-aggregating action, and can be used in biological and medical fields as, for example, an iron-supplementing agent, a contrast medium for X-ray imaging, a contrast medium for MRI, an exothermic medium for hyperthermia, an agent for blood stream measurement and a carrier used for concentrated administration of drugs to an affected part using a magnetic field.

What is claimed is:

1. A complex comprising a water-soluble carboxypolysaccharide selected from the group consisting of carboxydextran and carboxystarch, and magnetic iron oxide ultrafine particles having a particle diameter of about 2 to about 30 nm, the proportion of bivalent iron to total iron in the complex being in the range of 0 to about 7%, the complex having a magnetism of 10–150 emu per g of iron at 1 T; wherein said complex is prepared by oxidation with an oxygen-containing gas at a temperature of about 60° to 100° C. for about 2 to about 16 hours, or with an aqueous hydrogen peroxide at a temperature of about 0° to about 80° C. for about 10 minutes to about 24 hours.

2. The complex according to claim 1, wherein the water-soluble carboxypolysaccharide is carboxydextran.

3. The complex according to claim 1 wherein the water-soluble carboxypolysaccharide has a molecular weight of 500–300,000.

4. The complex according to claim 1 wherein the water-soluble carboxypolysaccharide has a molecular weight of 1,000–50,000.

5. The complex according to claim 1 wherein the complex is oxidized in the form of an aqueous sol.

6. The complex according to claim 1, wherein the oxygen-containing gas is a member selected from the group consisting of oxygen gas and air.

7. A contrast medium for use in magnetic resonance imaging, which comprises the complex according to claim 1.

8. A magnetic resonance imaging method which comprises administering an effective amount of the complex according to claims 1 to a patient and conducting magnetic resonance imaging.

* * * * *